United States Patent [19]

Shlenker et al.

[11] Patent Number: 5,130,159

[45] Date of Patent: Jul. 14, 1992

[54] MEMBRANES FASHIONED FROM LATEX AND OTHER MATERIALS AND METHODS OF PRODUCING THE SAME

[76] Inventors: Robin R. T. Shlenker, 2165 E. Alameda, Denver, Colo. 80209; Clive C. Solomons, 164 S. Fairfax St., Denver, Colo. 80222

[21] Appl. No.: 536,772

[22] Filed: Jun. 12, 1990

Related U.S. Application Data

[63] Continuation-in-part of Ser. No. 482,978, Feb. 22, 1990, Pat. No. 5,045,341, which is a continuation-in-part of Ser. No. 246,337, Sep. 19, 1988, Pat. No. 4,935,260, which is a continuation-in-part of Ser. No. 143,184, Jan. 13, 1988, Pat. No. 4,919,966, which is a continuation-in-part of Ser. No. 74,629, Jul. 17, 1987, Pat. No. 4,771,482.

[51] Int. Cl.$^5$ .............................. A01N 1/02
[52] U.S. Cl. .............................. 427/2; 2/167; 2/168; 128/844; 523/122
[58] Field of Search .............. 2/159, 161 R, 167, 168; 128/844; 427/2; 604/349, 353; 523/122

[56] References Cited

U.S. PATENT DOCUMENTS

| | | | |
|---|---|---|---|
| 4,675,347 | 6/1987 | Mochizuki et al. | 106/16 X |
| 4,853,978 | 8/1989 | Stockum | 2/167 |
| 4,867,968 | 9/1989 | Allen | 604/96 X |
| 4,876,293 | 10/1989 | Durney et al. | 524/533 X |
| 4,881,277 | 11/1989 | Hogle | 2/169 |
| 4,901,372 | 2/1990 | Pierce | 2/167 |
| 4,930,522 | 6/1990 | Busnel et al. | 128/844 |
| 5,019,096 | 5/1991 | Fox et al. | 427/387 X |

OTHER PUBLICATIONS

"A Method for Hydron Impregnation of Silicone Rubber" by Paul Predecki, J. Biomed. Mater. Res. vol. 8 (1974), pp. 487–489.
C. L. Fox Abstracts.

*Primary Examiner*—Michael Lusignan

[57] ABSTRACT

Various methods of forming a chemical barrier against the transmission of disease-causing microbes and other harmful agents through a membrane fashioned of latex or other material. In one method, the latex material is provided with microbe sterilization properties by deforming the latex material from a relaxed condition such that the pores therein are deformed, then washing the deformed latex material with a biocide, which is entrapped in the pores, and then relaxing the latex material. Alternatively, instead of washing the deformed latex material with the biocide, the biocide may be mixed directly with the liquid latex preferably along with a buffer agent and then the liquid latex can be cured. In yet another method, the latex material is treated with a silicone, protein or high molecular polyion to form a water resistant surface. A method of inhibiting the deterioration, extending the effective life, increasing the strength, and increasing the elasticity of the latex material is to mix an oxidation reducing agent that chelates iron and other heavy metals with the liquid latex and then to cure the latex. The latex materials produced by the foregoing methods are also disclosed.

34 Claims, 1 Drawing Sheet

MEMBRANES FASHIONED FROM LATEX AND OTHER MATERIALS AND METHODS OF PRODUCING THE SAME

BACKGROUND OF THE INVENTION

This patent application is a continuation-in-part of U.S. patent application Ser. No. 482,978 filed on Feb. 22, 1990 for "Covering Such As A Suit, Glove, Condom Or Sheath Forming A Chemical Barrier Against Harmful Agents And Methods Of Making The Same", now U.S. Pat. No. 5,045,341, which in turn is a continuation-in-part of U.S. patent application Ser. No. 246,337 filed on Sep. 19, 1988 for "Covering Such As A Suit, Glove, Condom Or Sheath Forming A Chemical Barrier Against Harmful Agents And Method Of Making The Same", now U.S. Pat. No. 4,435,260, which in turn is a continuation-in-part of U.S. patent application Ser. No. 143,184, filed Jan. 13, 1988 for "Covering Such As A Glove, Condom Or Sheath For Inhibiting The Spread Of Contagious Diseases And Methods Of Making And Using The Same", now U.S. Pat. No. 4,919,966, which in turn is a continuation-in-part of U.S. patent application Ser. No. 074,629, filed on Jul. 17, 1987, for "Glove For Inhibiting The Spread Of Contagious Diseases And Method Of Using The Same", now U.S. Pat. No. 4,771,482. All of these applications are owned by the same Applicant. The subject matter of the foregoing patent applications and patent is hereby incorporated by reference.

Latex materials have long been used as gloves and condoms for the purpose of inhibiting the transmission of disease producing microbes and other harmful agents. Both the chemical inertness and the physical density of latex make it difficult for molecules and microbes to pass through the structure of the latex material. Nevertheless, latex materials are known to possess imperfections in the form of pits, pores, and holes, which can facilitate the transmission of such microbes and harmful agents through the latex material.

The present invention relates to the desireable goal of forming a chemical barrier against the transmission of such microbes and other harmful agents through a membrane such as latex.

SUMMARY OF THE INVENTION

The present invention relates to various methods of forming a chemical barrier against the transmission of disease-causing microbes and other harmful agents through a membrane such as latex. In one method, the latex material is provided with microbe sterilization properties potentially by deforming the latex material from a relaxed condition such that the pores therein are deformed, then washing the deformed latex material with a biocide, which is entrapped in the pores, and then relaxing the latex material. Alternatively, instead of washing the deformed latex material with the biocide, the biocide may be mixed directly with the liquid latex preferably along with a buffer agent and then the liquid latex can be cured. In yet another method, the latex material is treated with a silicone, protein or high molecular polyion to form a water resistant surface. A method of inhibiting the deterioration, extending the effective life, increasing the strength, and increasing the elasticity of the latex material is to expose the latex material to either a chelating agent or an oxidation reducing agent that inhibits the action of iron and other heavy metals with the liquid latex and then to cure the latex. The invention also relates to the latex materials produced by the foregoing methods.

BRIEF DESCRIPTION OF THE DRAWINGS

The invention will be described with reference to the accompanying drawings, wherein.

DESCRIPTION OF A PREFERRED EMBODIMENT

Figure 1:
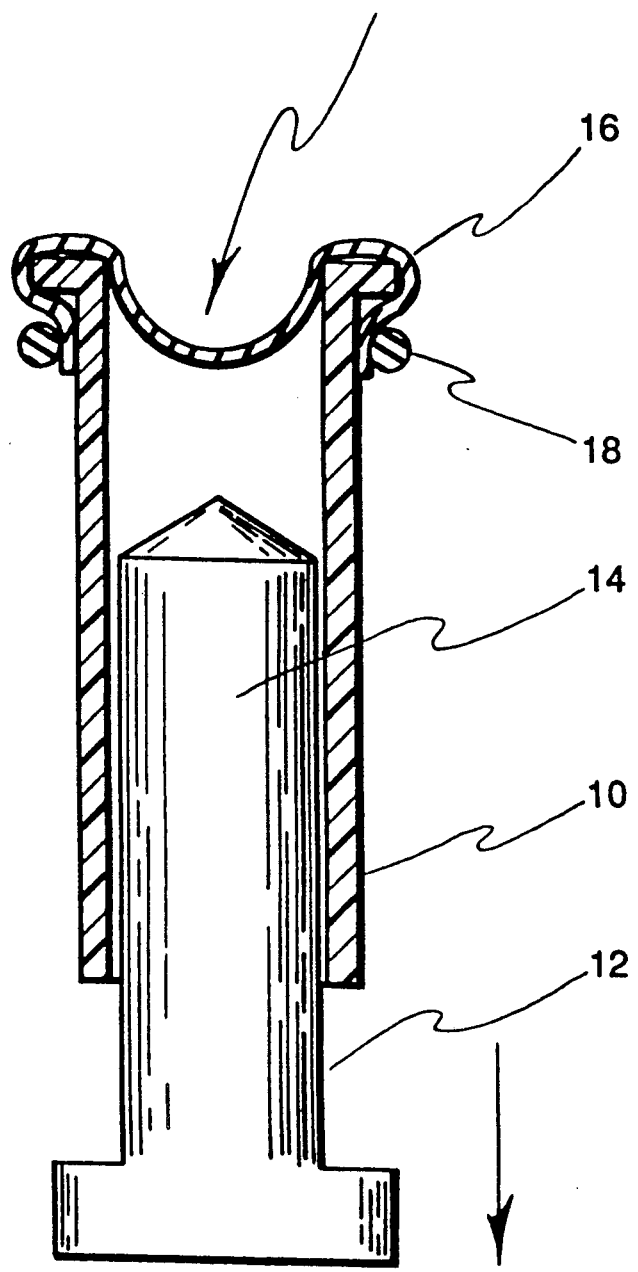
FIG. 1 is a cross-sectional view of a syringe device used to deform the latex material in accordance with the methods of one embodiment of the present invention.

The present invention relates to methods of forming a chemical barrier against disease-causing microbes and other harmful agents through a membrane fashioned of latex or another material such as natural skin, natural rubber, solvent cast membranes, elastomers, and polymers. For convenience, the preferred embodiment will be described with reference to a latex material. The latex material may be fashioned as a glove, condom, diaphragm, slipper, overshoe, sterile bands, catheters, latex or plastic tubing, diaphragms, drapes, gut openings, mouthpieces, baby nipples, intra gastric nasal tubes, nasal gastric tubes, kidney shunts, rubber dams for teeth, plastic braces for teeth, sub-clavian vein and artery shunts, colostomy bags, or any other product. Normally these latex products will be adapted for use in juxtaposition to a person's or animal's skin.

One method of inhibiting the transmission of disease-causing microbes and harmful agents through the latex material is to entrap a biocide within the pits and pores of the latex materials. As used in the instant patent application, the term "biocide" means that the disease-producing characteristic or harm-causing characteristic is rendered ineffective substantially upon contact or shortly after the microbe or harmful agent contacts the biocide material. A few suitable biocides are believed to be dextran sulphate, nonoxynol-9, benzalkonium, betadyne, gentian violet, acriflavine and acridine dyes, mercurochrome, silver salts, and an extract of blue green algae. Additionally, a very lengthy list of what are believed to be suitable biocides is being filed concurrently with this patent application and forms part of the file wrapper.

The biocide may be applied to the latex material by pouring at least 500 ml of an aqueous solution of the biocide into a glove or condom and allowing to stand for five to twenty minutes at twenty to thirty degrees Celsius. The solution is removed, and the glove washed several times with water to remove excess biocide. Ethylene diamine tetra-acetic acid (EDTA) in tris buffer pH 8.5 can also be present during treatment with biocide in order to decrease degradative oxidation catalyzed by metal ions such as iron, copper and manganese. Deformation of the glove or condom is desireable for uniform uptake of biocide. When dealing with thicker materials, it might be necessary to use air pressure or other suitable forces to obtain a one to three-fold stretching of the material.

It should be appreciated that more than one biocide may be applied to the latex material either simultaneously as a mixture or sequentially.

The latex material may be deformed mechanically by stretching the latex material. In an experiment, a syringe, as shown in FIG. 1, has been used effectively to mechanically deform latex material for the purpose of applying a biocide. The syringe includes a generally cylindrical barrel 10 and a plunger 12. A cylindrical piston 14 forming a part of the plunger 12 is adapted to be slideably, tightly received within the barrel 10. A piece of latex material 16 is disposed completely over an end of the barrel 10, on the barrel end opposite the plunger 12. The latex material 16 is retained in such a position by means of a rubberband 18, which serves to clamp the edges of the latex material 16 to the outside peripheral surface of the barrel 10 in the region adjacent to the barrel end. It will be appreciated that movement of the plunger 12 in either direction will distend the latex material 16 due to the pressure differential created across the latex material 16. The biocide (preferably in liquid form, but potentially in powder, gelatin, paste, foam or other fluid form) may be applied to the latex material 16 on either side or both sides of the latex material 16. Other mechanical means of deforming and stretching the latex material include placing the biocide within a glove, condom or the like either under pressure or permitting the pull of gravity to cause the distention. Also, the interior of a glove, condom, etc. may be subjected to air, water, or other fluid pressure and the outside of the glove may be in intimate contact with the biocide.

The amount of biocide trapped within the pores of the latex material depends upon several factors: the size and number of pores in the latex material, the degree of distention or deformation of the latex material, the concentration of the biocide, whether buffers and chelating agents are present in the liquid latex, and the length of time in which the biocide is in contact with the deformed latex material. Experiments have been conducted using gentian violet and acriflavine dyes as the biocides. These experiments, in combination with theoretical calculations, indicate that the gentian violet molecules, on the average, are only 2.7 angstroms apart within the latex material and that there are over 400,000 molecules of gentian violet within a volume of latex material equivalent to the effective size of a viral particle such as HIV (AIDS) or hepatitis B.

In one experiment, an ANSELL brand latex glove was hung vertically and stretched by the gravitational pull of the weight of the liquid biocide. Thereafter, the latex material was soaked in a mixture of 600 milliliters of a 0.3 mg/ml solution of gentian violet for twenty minutes. The latex material was then relaxed, washed and dried. The latex material, which initially was colored white, had turned purple—the color of the gentian violet.

The amount of biocide taken up by skin membrane was substantially greater than that found for latex membranes.

Instead of adding the biocide to the latex material after the latex material has been cured, the biocide may be added to the liquid latex material prior to curing. This method includes the steps of mixing the liquid latex material with the biocide and a buffer agent consisting of TRIS or citrate prior to curing. In one experiment, 100 ml of an aqueous solution of acriflavine and acridine containing EDTA and tris buffer were added to 500 ml of liquid glove latex. After forming the latex shape, the latex was cured in the normal way.

The transmission of disease-causing microbes and harmful agents through the latex material may also be inhibited by treating the surface of the latex material such that the latex surface material is substantially water resistant or sealed. The treated latex material may or may not have the biocide already entrapped therein. If the biocide is susceptible to leaching from the latex material (for example, gentian violet is susceptible to leaching if subjected to alcohol), then such surface treating is desireable when the biocide is entrapped within the latex material. Nevertheless, the sealed or water resistant surface also inhibits the transmission of the microbes and other harmful agents regardless of whether a biocide is also present. The latex material surface may be coated with silicone, proteins, and high molecular weight polyions to form the sealed or water resistent surface. Suitable coating materials are gelatin, silicones, albumium, casein, dextrins, adhesives, and soybean proteins. The treated region of the latex material surface that is sealed and water resistent is approximately 5-10 mils thick.

It has been observed that the addition of one or more biocides, especially acriflavine, to the latex material enhances the strength of the latex material.

The properties of latex materials also deteriorate over time, thereby increasing the number and size of the pits and pores in the latex material and otherwise increasing the transmission characteristics of the latex material. It is believed that the deterioration of latex material over time is catalyzed by oxidation by ozone facilitated by the presence of iron and other heavy metals such as copper and manganese entrained within the latex material. Accordingly, the properties of latex according to the present invention may be enhanced by using traditional techniques of mixing of liquid latex with an oxidation reducing agent that chelates iron and other heavy metals. A suitable oxidation reducing agents are ethylene diamine tetra acetic acid (EDTA), disodium salt and/or citric acid monosodium salt. Numerous metal-chelating agents are available for this purpose. It is believed that the addition of the oxidation reducing agent also increases the strength and elasticity of the latex material and retards aging.

The membranes fashioned from latex or other material resulting from the foregoing methods are also within the scope of the present invention.

Although particular embodiments of the present invention have been described and illustrated herein, it should be recognized that modifications and variations may readily occur to those skilled in the art and that such modifications and variations may be made without departing from the spirit and scope of our invention. Consequently, our invention as claimed below may be practiced otherwise than as specifically described above.

We claim:

1. A method of making a latex membrane having a biocide barrier comprising the steps of:
   providing a deformable latex membrane having pores;
   deforming the membrane from a relaxed condition such that the pores therein are concomitantly deformed;
   treating the deformed membrane with a biocide; and
   relaxing the membrane.

2. A method of making a latex membrane having a biocide barrier according to claim 1 comprising the further step of washing excess biocide from the surface of the membrane.

3. A method of making a latex membrane having a biocide barrier according to claim 2 wherein said biocide is disposed substantially uniformly and substantially only in the pores after the membrane has been washed.

4. A method of making a latex membrane having a biocide barrier according to claim 1 wherein the biocide is selected from the group consisting of dextran sulphate, nonoxynol-9, benzalkonium, betadyne, gentian violet, acriflavine and acridine dyes, mercurochrome, silver salts, and an extract of blue-green algae.

5. A method of making a latex membrane having a biocide barrier according to claim 1 wherein the membrane is deformed by mechanically stretching the membrane.

6. A method of making a latex membrane having a biocide barrier according to claim 1 wherein said biocide substantially uniformly fills the pores.

7. A method of making a latex membrane having a biocide barrier according to claim 1 having improved strength characteristics comprising the further step of treating the deformed membrane with a chelating agent.

8. A method of making a latex membrane having a biocide barrier according to claim 7 wherein said chelating agent comprises EDTA.

9. A method of making a latex membrane having a biocide barrier according to claim 1 having improved aging characteristics comprising the further step of treating the deformed membrane with a chelating agent.

10. A method of making a latex membrane having a biocide barrier according to claim 9 wherein said chelating agent comprises EDTA.

11. A method of making a latex membrane having improved strength characteristics comprising the steps of:
providing a deformable latex membrane having pores;
deforming the membrane from a relaxed condition such that the pores therein are concomitantly deformed;
treating the deformed membrane with a chelating agent; and
relaxing the membrane.

12. A method of making a latex membrane according to claim 11 wherein said chelating agent comprises EDTA.

13. A method of making a latex membrane having improved aging characteristics comprising the steps of:
providing a deformable latex membrane having pores;
deforming the membrane from a relaxed condition such that the pores therein are concomitantly deformed;
treating the deformed membrane with a chelating agent; and
relaxing the membrane.

14. A method of making a latex membrane according to claim 13 wherein said chelating agent comprises EDTA.

15. A method of making a latex membrane having improved strength characteristics, said membrane formed by curing a liquid latex material, said method comprising the steps of:
providing a liquid latex material;
providing a chelating agent;
providing a buffer agent selected from the group consisting of TRIS and citrate;
mixing the liquid latex material, the buffer agent and the chelating agent; and
curing the latex material.

16. A method of making a latex membrane according to claim 15 wherein said chelating agent comprises EDTA.

17. A method of making a latex membrane having improved strength characteristics, said membrane formed by curing a liquid latex material, said method comprising the steps of:
providing a liquid latex material;
providing a chelating agent;
providing a buffer agent selected from the group consisting of TRIS and citrate;
mixing the liquid latex material, the buffer agent and the chelating agent; and
curing the latex material.

18. A method of making a latex membrane according to claim 17 wherein said chelating agent comprises EDTA.

19. A method of making a latex membrane having a biocide barrier, said membrane formed by curing a liquid latex material, said method comprising the steps of:
providing liquid latex material;
providing a biocide;
providing a buffer agent selected from the group consisting of TRIS and citrate capable of acting as a buffer between the biocide and the latex;
mixing the liquid latex material, the buffer agent, and the biocide; and
curing the latex material.

20. A method of making a latex membrane having a biocide barrier according to claim 19 wherein the biocide is selected from the group consisting of dextran sulphate, nonoxynol-9, benzalkonium, betadyne, gentian violet, acriflavine and acridine dyes, mercurochrome, silver salts, and an extract of blue-green algae.

21. A method of making a latex membrane according to claim 19 having improved strength characteristics comprising the further steps of providing a chelating agent and mixing the liquid latex material and the chelating agent.

22. A method of making a latex membrane according to claim 21 wherein said chelating agent comprises EDTA.

23. A method of making a latex membrane according to claim 19 having improved aging characteristics comprising the further steps of providing a chelating agent and mixing the liquid latex material and the chelating agent.

24. A method of making a latex membrane according to claim 23 wherein said chelating agent comprises EDTA.

25. A method of making a polymeric covering adapted for placement adjacent to a human body comprising the steps of:
providing a latex polymeric covering having pores;
deforming the covering from a relaxed condition such that the pores therein are concomitantly deformed;
treating the deformed covering with a biocide;
relaxing the covering; and
coating the surface of the polymeric covering with a chemical selected from the group consisting of gelatin, albumium, casein, dextrins, silicone, adhesives and soybean protein such that the surface of the covering is substantially sealed and water resistant.

26. A method of making a polymeric covering according to claim 25 wherein said treated surface is substantially between five to ten mils thick.

27. A membrane comprising a latex material having a substantially water resistant surface treated with a chemical selected from the group consisting of gelatin, albumium, casein, dextrins, adhesives and soybean protein.

28. A membrane according to claim 27 wherein said water resistant treated surface is substantially between five to ten mils thick.

29. A method of making an animal skin membrane having a biocide barrier comprising the steps of:
providing a deformable animal skin membrane having pores;
deforming the membrane from a relaxed condition such that the pores therein are concomitantly deformed;
treating the deformed membrane with a biocide; and
relaxing the membrane.

30. A method of making an animal skin membrane according to claim 29 wherein said biocide substantially uniformly fills the pores.

31. A method of making an animal skin membrane having a biocide barrier according to claim 29 comprising the further step of washing excess biocide from the surface of the membrane.

32. A method of making an animal skin membrane according to claim 31 wherein said biocide is disposed substantially uniformly and substantially only in the pores after the membrane has been washed.

33. A method of making an animal skin membrane having a biocide barrier according to claim 29 wherein the biocide is selected from the group consisting of dextran sulphate, nonoxynol-9, benzalkonium, betadyne, gentian violet, acriflavine and acridine dyes, mercurochrome, silver salts, and an extract of blue-green algae.

34. A method of making an animal skin membrane having a biocide barrier according to claim 29 wherein the membrane is deformed by mechanically stretching the membrane.

* * * * *